United States Patent [19]
Goffin et al.

[11] Patent Number: 5,290,353
[45] Date of Patent: Mar. 1, 1994

[54] VATERITE AND PRODUCTION METHOD

[75] Inventors: Robert Goffin, Trooz, Belgium; Henri-René Langelin, Caffiers, France

[73] Assignee: Lhoist Recherche et Developpement S.A., Belgium

[21] Appl. No.: 969,295

[22] PCT Filed: Jul. 23, 1991

[86] PCT No.: PCT/BE91/00051
§ 371 Date: Jan. 22, 1993
§ 102(e) Date: Jan. 22, 1993

[87] PCT Pub. No.: WO92/01629
PCT Pub. Date: Feb. 6, 1992

[30] Foreign Application Priority Data
Jul. 24, 1990 [BE] Belgium ............................ 09000743

[51] Int. Cl.$^5$ .................................................. C09C 1/02
[52] U.S. Cl. ...................... 106/464; 106/465; 423/430; 423/432
[58] Field of Search .............. 106/464, 465; 423/165, 423/430, 432, 637, 640

[56] References Cited
U.S. PATENT DOCUMENTS

| | | | |
|---|---|---|---|
| 3,304,154 | 2/1967 | Kiouzes-Pezas | 423/432 |
| 4,871,519 | 10/1989 | Zikmund et al. | 423/169 |
| 5,232,678 | 8/1993 | Bleakley et al. | 423/432 |

FOREIGN PATENT DOCUMENTS

| | | |
|---|---|---|
| 0140644 | 5/1985 | European Pat. Off. |
| 0197327 | 10/1986 | European Pat. Off. |
| 3619909A1 | 12/1987 | Fed. Rep. of Germany |
| 2405903 | 5/1979 | France |

OTHER PUBLICATIONS

Chemical Abstract for "Manufacture of Hexagonal Plate-Shaped Calcium Carbonate Powder", Tanaka et al. JP 62-113,718 May 25, 1987.
Chemical Abstract for "Production of Cubic Calcium Carbonate", Hideo et al. Sep. 30, 1986 JP 61-219,716.

*Primary Examiner*—Karl Group
*Assistant Examiner*—Chris Gallo
*Attorney, Agent, or Firm*—Charles D. Gunter, Jr.

[57] ABSTRACT

The present invention relates to a process for the preparation of substantially spherical monocrystalline vaterite, in particular, of vaterite having a determined size.

21 Claims, 2 Drawing Sheets

VATERITE AND PRODUCTION METHOD

In the process according to the invention, calcium oxide or hydroxyde is treated in a reaction medium containing an acid salt of an orgnic amine so as to obtain a medium having a pH of treatment higher than 10 and a calcium content form 0.35 to 0.65 mole/litre, $CO_2$ is introduced under stirring up to the obtention of a pH equal to about the pH of treatment and $CO_2$ is introduced in the medium at a rate lower to 50 g $CO_2$/hour/litre.

The invention relates also to a vaterite having a spherical shape with two diametrically opposite hollows and a grain size distribution factor lower than 0.5.

STATE OF THE ART

FR-A-2298511 discloses a process for the preparation of vaterite In this known process, calcium oxide is treated in a reaction medium containing nitrates or chlorides and an amine, insoluble compounds are removed from the medium and $CO_2$ are introduced in the medium so as to precipitate calcium carbonate in the form of aggregates of vaterite particles. The so obtained vaterite is not stable and does not allow the preparation of calcium derivates of very high purity, for example having a purity higher than 99,99%. Moreover, it is only possible to obtain by means of this process a mixture of vaterite, the grain size distribution factor of which is higher than 1.

A process allowing the preparation of calcium carbonate of high purity (higher than 99%) is known by U.S. Pat. No. 4,871,519. In this process, decarbonated dolomitic lime is treated in a solution containing an acid salt of an organic amine so as to convert calcium into soluble salt and after filtration, the solution is treated by means of $CO_2$ so as to precipitate calcium carbonate.

All the examples of this document do not allow to obtain stable vaterite, in particular a vaterite having a grain size distribution factor less than 1.

Grain size distribution factor is a parameter allowing to determine the size repartition of a mixture of particles. An important size distribution factor means that the mixture contains an important amount of particles the size of which differs from the mean size.

The grain size distribution factor of a mixture may be calculated by the following formula:

$$2 \times \frac{d_{80\%} - d_{20\%}}{d_{80\%} + d_{20\%}}$$

in which
$d_{80\%}$ is the upper diameter of the particles of the fraction of the mixture passing at 80%
$d_{20\%}$ is the upper diameter of the particles of the fraction of the mixture passing at 20%
fraction passing at x%
is the fraction containing the particles of the mixture having a size lower than a determined value, this fraction corresponding to x% by weight of the mixture.

BRIEF DESCRIPTION OF THE INVENTION

The present invention relates to a process for the preparation of substantially spherical vaterite.

Another subject matter of the present invention is a vaterite in the form of particles, the grain size distribution factor of which is less than 1, preferably than 0.5.

In particular, the invention relates to a vaterite having a size lower than $20\mu$, advantageously than 10 microns. In a preferred form, the vaterite according to the invention has a mean diameter (mean by weight) lower than $5\mu$, advantageously than $3\mu$ and especially lower than $1\mu$.

The process according to the invention, especially the preparation process for obtaining a substantially spherical vaterite, not in the form of aggregates of particles, for example a vaterite in the form of particles having a grain size distribution factor less than 1, advantageously than 0.5, comprises the following steps:

a mixture of particles containing calcium in the form of calcium oxide and/or hydroxide is treated in a reaction medium containing an acid salt of an organic amine so as to convert the calcium into a soluble salt and so as to obtain a medium, the pH of which, called pH of treatment, has a value higher than 10;

$CO_2$ is introduced in the medium under stirring up to the moment when the pH of the medium reaches a pH called pH of saturation, the value of which is about $0.83 \times$pH of treatment (so as to have a $CO_2$ saturation of the medium), and $CO_2$ is introduced in the medium which is possibly stirred at a rate lower than 50 g $CO_2$/hour/liter so as to form substantially spherical vaterite especially having a predetermined size.

According to a characteristic of this process $CO_2$ is introduced in the medium when the $CO_2$ content of the medium is comprised between 0.3 and 1, advantageously between 0.35 and 0.65, preferably between 0.45 and 0.55 mole/liter.

The process may possibly comprise a step in which the Ca content is adjusted before the introduction of $CO_2$ into the medium.

According to another characteristic, a mixture of particles containing CaO is treated in the reaction medium at a temperature lower than 50°–60° C., preferably lower than 20° C.

Advantageously, $CO_2$ is introduced in the medium when the temperature of the medium is lower than 40° C. and preferably than 20° C. In an embodiment which is preferred when the mixture of particles containing calcium also contains impurities such as magnesium derivatives (MgO, Mg(OH)$_2$), insoluble compounds are removed from the medium after the treatment of the mixture in the reaction medium. Said removal may be made by filtration, decantation, etc.

For improving the removal of impurities, applicant has observed that it was useful to treat the mixture of particles containing calcium in a reaction medium containing an acid salt of an organic amine in presence of silica and possibly of an additive such as a porous carrier, zeolithes, alumina, iron and iron derivatives.

The weight ratio $SiO_2$/CaO or Ca(OH)$_2$ is comprised between 0.5 and 10, while the weight ratio of iron and/or alumina/CaO or Ca(OH)$_2$ is advantageously less than 0.1, preferably comprised between 0.005 and 0.03.

In a preferred embodiment, $CO_2$ is introduced in the medium in three steps, namely:
1. introduction of $CO_2$ so as to lower the pH up to a pH -called pH of saturation-, the value of which is about $0.83 \times$pH of treatment.

2. introduction of $CO_2$ at a rate lower then 50, advantageously than 20 g $CO_2$/hour/liter so as to lower the pH to a pH called pH of nucleation, the value of which is about 0.8×pH of treatment, and
3. introduction of $CO_2$ at a rate lower than 50, advantageously than 20 g $CO_2$/hour/liter so as to lower the pH to a pH called pH of cristallization, the value of which is less than 0.75×pH of treatment, preferably comprised between 0.7 and 0.75 pH of treatment.

The pH of nucleation advantageously corresponds to about 0.97 x pH of saturation, while the pH of cristallization is advantageously less than 0.93×pH of nucleation.

Advantageously, the introduction of $CO_2$ in the medium is stopped between said three steps.

According to a characteristic of this embodiment the reaction medium is subjected to a pressure higher than $2\ 10^5$ Pa for the first step of introduction of $CO_2$ in the medium. For this first step, the flow rate of $CO_2$ in the medium is advantageously higher than 50g $CO_2$/hour/liter.

According to other details of the process according to the invention, the medium is submitted to a vigourous stirring for the first step of introduction of $CO_2$ and to a moderous stirring for the second and third steps of introduction of $CO_2$.

Vigourous stirring means a stirring characterized by a Reynolds number higher than 8000, while moderous stirring mean a stirring characterized by a Reynolds number lower than 5000, but preferably greater than 10.

This Reynolds number may be calculated by the following formula:

$$Re = Da^2\, N\, \rho/\mu$$

in which
Re: Reynolds number
Da: diameter of the agitator (m)
$\rho$: density of the medium (kg/m$^3$)
$\mu$: viscosity (Pa s$^{-1}$)

A Reynolds number greater than 10000 corresponds to a turbulent movement in the medium, while a Reynolds number lower than 10 corresponds to a laminar movement.

The acid salt of an organic amine is preferably a compound of general formula 1:

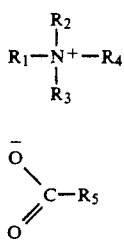

in which
at least $R_1$ or $R_2$ or $R_3$ or $R_4$ is a hydrocarbon group which is advantageously substituted by at least one hydroxyl group.

Preferably, radicals $R_1$, $R_2$, $R_3$, $R_4$ and $R_5$ have the following meanings:
$R_1$ is a hydrocarbon radical substituted by at least one hydroxyl group, this radical having from 1 to 10 carbon atoms;
$R_2$, $R_3$ and $R_4$ are hydrogen or a hydrocarbon radical possibly substituted by one or more hydroxyl groups, this hydrocarbon radical having advantageously 1 to 10 carbon atoms, and
$R_5$ is hydrogen or a $C_1$-$C_{10}$ hydrocarbon radical possibly substituted by one or more hydroxyl or carboxyl groups.

Preferably, $R_1$ is a linear or branched group substituted by at least one hydroxyl group. For example, $R_1$ may be selected among: ethyl, hydroxymethyl, 2-hydroxyethyl, 1-hydroxyethyl, 3-hydroxypropyl, 2-hydroxypropyl, 1-hydroxypropyl, 4-hydroxybutyl, 3-hydroxybutyl, 2-hydroxyisobutyl, 3-hydroxy-2-methylpropyl, 5-hydroxypentyl, 3-hydroxymethylbutyl, 2-hydroxyisopentyl, 3-hydroxy-1,1-dimethylpropyl, 3-hydroxy-1,2-dimethylpropyl;

$R_2$, $R_3$ and $R_4$ are advantageously a hydrogen atom or a methyl, ethyl, hydroxyethyl, propyl or a hydroxypropyl group;

$R_5$ is advantageously a hydrogen atom or a $C_1$-$C_5$ radical. preferably, the group $-OOC-R_5$ is the rest of an acid selected among formic acid, acetic acid, citric acid propanoic acid, pentanoic acid, methylproprionic acid, dimethylpropanoic acid, methylbutanoic acid, or a mixture thereof.

As example of compound of formula 1, diethylamino acetate or formate and monoethanolamino acetate or formate may be mentioned.

When y is the number of acid functions of the compound, the molar ratio calcium oxide/compound of formula 1 is greater than 0.1 and is preferably comprised between 0.5 y and 1 y. Advantageously, this molar ratio is about 0.6 y.

Other particularities and details of the invention will appear from the following detailed description in which reference is made to examples of preparation as well as the here attached drawings.

BRIEF DESCRIPTION OF DRAWINGS

In these drawings.

DESCRIPTION OF THE EXAMPLES

Example 1

An aqueous reaction medium has been prepared by mixing a formic acid ethanolamine ester (an aminoalcohol ester of formula $CH_2OH\ CH_2NH_3COOH$) so as to obtain a reaction medium having a concentration of 1 mole ester per liter. Powder of lime CaO has then been added to the reaction medium at a rate of 0.5 mole per liter of reaction medium. (Molar ratio Ca/ester: 0.5).

The temperature of the reaction medium has been maintained to 20° C. during this quick treatment of the lime.

The following reaction occured:

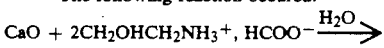

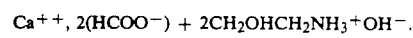

The pH of the reaction medium has varied during this reaction from about 6 to about 11.5-12.

The reaction medium has then been filtered by means of a precoated filter so as to remove metallic impurities which at such a pH precipitate. So, it was possible to remove all traces of aluminium, iron and heavy metals.

After filtration, $CO_2$ was bubbled through the reaction medium, the Ca concentration of which was about 0.5, (temperature of the medium: 20° C.).

This bubbling has been made in the following manner:

In a first step, gazeous $CO_2$ has been introduced into the medium at a rate of 70 g $CO_2$/hour/liter of medium so as to lower the pH of the medium up to a value of about 9.8. This operation has been made in a vessel under a pressure of 2 to 3 $10^5$ Pa and submitted to the action of an anchor agitator. Said agitator had a diameter of 60 mm while its rotation speed was 500-600 rounds/minute. The cylindrical vessel had a diameter of 200 mm (volume of the reactor: 2 liters).

The movement created by the agitator in the vessel was substantially turbulent.

When the pH of the medium was about 9.8, the feeding of $CO_2$ has been stopped and the medium was no more maintained under pressure, nor subjected to the action of the agitator for a few minutes.

Gazeous $CO_2$ has then been introduced or fed into the reaction medium at a rate of 10-15 g $CO_2$/hour/litre so as to lower the pH of the medium to 9.5-9.6. The vessel containing the reaction medium was not pressurized. When introducing said $CO_2$, the reaction medium was submitted to a moderate agitation, the rotation speed of the blades being 100 rounds/minute.

When the pH of the medium was about 9.5-9.6, the feed of $CO_2$ was stopped for a few minutes, while maintaining the medium under a moderate agitation (rotation speed: 100 rounds/minute).

Finally, $CO_2$ has been introduced into the solution maintained under moderate agitation at a rate of 10-15 g $CO_2$/hour/liter of solution (rotation speed 100 rounds/minute) up to the lowering of the pH to a value of about 8.5.

Vaterite precipitated, was recovered by filtration and was washed by means of a solution containing 50% by weight water and 50% by weight methanol.

Figure 1:
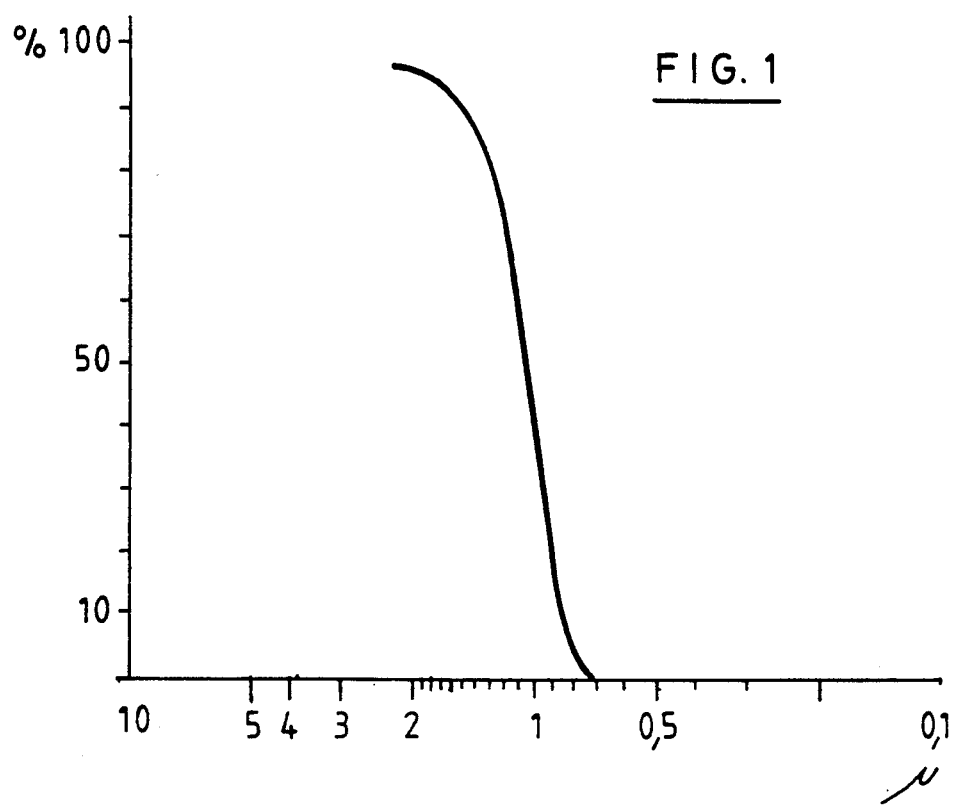
FIGS. 1 to 3 show the grain size distribution of vaterite obtained by a process according to the invention (undersize fraction in % by weight in function of the size expressed in and FIG. 4 is a cross section view, on enlarged scale of a vaterite grain prepared by a process according to the invention.

The grain size distribution factor of the so obtained vaterite is shown in FIG. 1.

This vaterite had the following characteristics:
purity higher than 99.99%
specific area 30 m²/g
stability in the reaction medium higher than 24 hours
mean size: 1μ
grain size distribution factor:

$$2 \times \frac{1.3 - 0.9}{1.3 + 0.9} = 0.36$$

Due to the bubbling of $CO_2$, the initial reaction medium has been formed again so that the latter may be used for treating a new amount of CaO.

Examples 2 and 3

Vaterite has been prepared in the manner described in example 1 except that in the second and third steps of introduction of $CO_2$ into the medium, the rotation speed of the agitator was respectively 125 and 150 rounds/minute.

Figure 2:
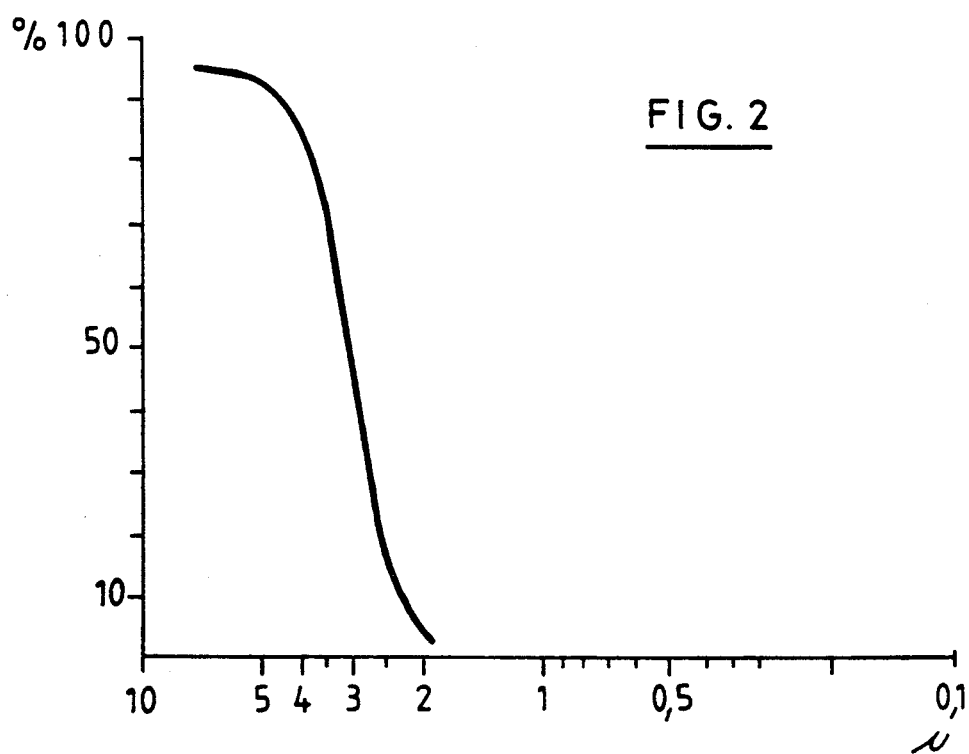
Figure 3:
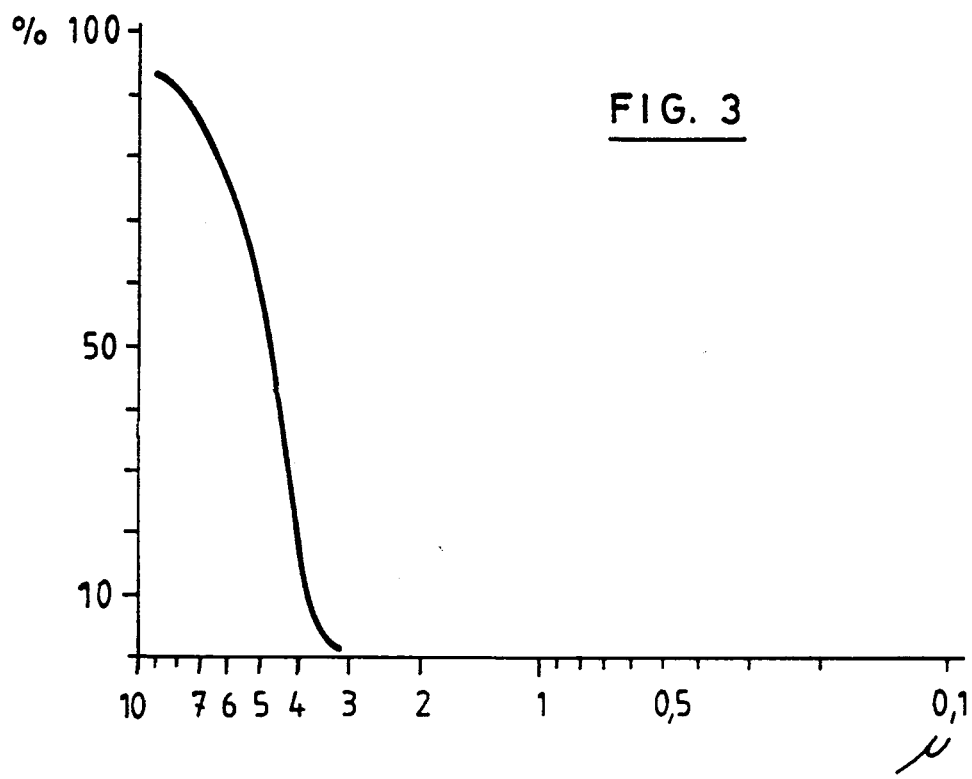

The grain size distribution of the so obtained vaterite is shown in FIG. 2 for a rotation speed of 125 rounds/minute for the second and third steps of introduction of $CO_2$ into the medium and in FIG. 3 for a rotation speed of 150 rounds/minute for the second and third steps of introduction of $CO_2$ into the medium.

The following table gives values characterizing the vaterite obtained in examples 1 to 3.

TABLE

| Rotation speed for the second and third steps | mean size μ | grain size distribution factor |
|---|---|---|
| 100 | 1 | 0.36 |
| 125 | 3 | 0.46 |
| 150 | 5 | 0.43 |

This table shows that it is possible by means of the process according to the invention to prepare a vaterite having a predetermined mean size, such as a vaterite having a grain size distribution factor less than 0.5 by selecting a rotation speed of the agitator, i.e. by selecting a movement which may be characterized by a determined Reynolds number.

Vaterite of example 1 has been calcined in an oven at a temperature of 1100° C. so as to obtain, as calcium derivative, extra pure lime CaO.

This extra pure calcium oxide had the following properties:
purity: more than 99.99 %
size: <20 microns
Aluminum: no trace has been found
Surfact BET: 20 m²/g During the burning, organic acids or salts thereof still present as trace into the vaterite are decomposed into $H_2O$, $CO_2$, i.e. in products which do not contaminate the calcium oxide.

Example 4

The method of example 1 has been repeated for the preparation of calcium carbonate and calcium oxide, except that
ethanolamino acetate has been used instead of ethanolamino formate,
that the temperature of the media was 40° instead of 20° C. when treating lime containing few dolomitic lime, and
that the bubbling of $CO_2$ into the filtered medium has been made in a vessel under pressure (2 $10^5$ Pascal).

The vaterite obtained by the process using ethanolamine acetate had the following properties:
purity: more than 99,99% $CaCO_3$
Aluminum: no trace found
Iron: no trace found
Heavy metals: no trace found
Specific surface: 25 m²/g

Examples 5 to 8

Example 1 has been repeated except that the calcium acetate concentration of the medium has been modified. The following table gives the results of these tests.

TABLE

| Example | Ca Concentration (mole/liter) | Remarks |
|---|---|---|
| 5 (Comparative example) | 0.75 | formation of vaterite as well as agglomerates of grains of vaterite |
| 6 | 0.5 | formation of spherical vaterite |
| 7 | 0.45 | formation of spherical vaterite |
| 8 | 0.3 | formation of |

TABLE-continued

| Example | Ca Concentration (mole/liter) | Remarks |
| --- | --- | --- |
| (Comparative example) | | crystals, the form of which is close to that of lentils |

This table shows that an appropriate selection of the Calcium concentration in the reaction medium allows to obtain by the process according to the invention a substantially spherical vaterite. Thus, in the process according to the invention, the Ca concentration in the medium is advantageously comprised between 0.35 and 0.65, preferably between 0.45 and 0.55 mole/litre.

Figure 4:
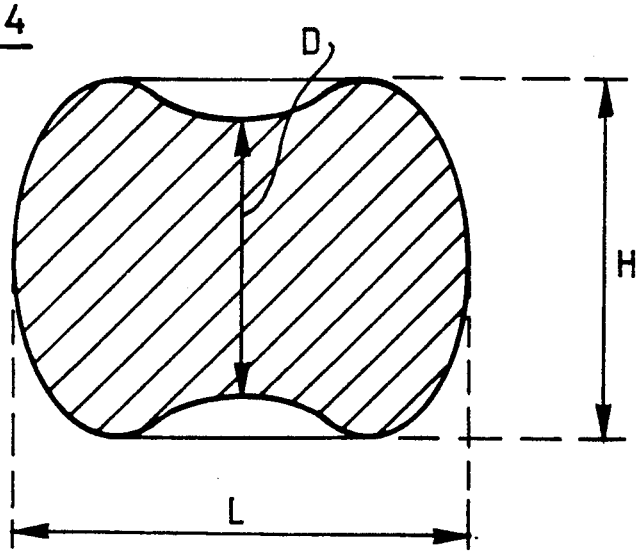

The vaterite prepared in examples 6 and 7 had the form of a sphere with two hollows which are diametrically opposite to each other, the height H of the vaterite in the direction of the diameter D which joins the two hollows corresponding to about 70% of the width of the vaterite measured in a plane perpendicular to said diameter. Such a vaterite is shown in cross-section in FIG. 4.

The stability of the vaterite according to the invention has been compared with that of a vaterite obtained by a known process. This study of the stability has been made by means of a scanning electron microscope (T 330 A-Japanese Electronical Optical Limited).

The results of this study have been given in the following table

TABLE

| | Vaterite according to the invention | Vaterite obtained by a known process |
| --- | --- | --- |
| after 10' | vaterite | vaterite |
| after 15' | vaterite | conversion into calcite |
| after 24 hours | vaterite | |

Example 9

The method of example 1 for the preparation of calcium carbonate has been repeated, except that particles of silica, alumina and iron have been added to the mixture of lime particles CaO. The weight ratio $SiO_2/CaO$ was 0.5, while the weight ratio iron and alumina/CaO was 0.01.

It has been observed hat the filtration step of the reaction medium was improved, so that it would be possible to remove impurities by a simple decantation. It was possible by adding such additives to obtain by decantation after 2 hours a clear solution. As comparison, when using no of said additives, it was not possible after 24 hours by decantation to obtain a clear solution.

The vaterite according to the present invention can be used for the preparation of:

a mixture of vaterite according to the invention (such a mixture may be characterized by the presence of many vaterites having a grain size distribution factor less than 1, preferably than 0.5);

a vaterite according to the invention having a layer of a metal selected among precious metals, especially gold, silver and platinum;

magnetic tapes comprising, for example 4% by weight of particles of vaterite having a metallized layer, a soap, detergent, tooth pasta or a cosmetic product containing a vaterite according to the invention;

a paper containing a vaterite according to the invention;

a glue containing a vaterite according to the invention;

a paint containing a vaterite according to the invention;

a coating slip for paper, said coating slip containing a vaterite according to the invention a lubricant made from a vaterite according to the invention;

a thixotropic agent (for soap . . . ) made from a vaterite according to the invention;

an agent for treating surface, said agent being made of a vaterite according to the invention;

a sealing powder for example in order to guarantee the sealing at connections of water pipe, said powder containing a vaterite according to the invention.

The vaterite according to the invention by means of its form and by means of its grain size distribution factor allows to obtain a good adhesion of particles to the glue or paint, but moreover allows to avoid the formation of a non regular layer of glue or paint. It also allows in the case of tooth pasta to avoid scratching of tooth, but further improves the removal of wastes, etc present on or between tooth. Such a removal is made during the brushing of the tooth but also during the rinsing.

It is obvious that if it is possible to obtain extra pure calcium carbonate, it is also possible to obtain extra pure calcium derivatives. As example only, the following calcium derivatives obtained by conversion of calcium carbonate prepared by the process according to the invention may be mentioned calcium oxide, calcium hydroxide, calcium chloride, calcium carbonate, calcium fluoride , calcium oxalate, calcium citrate, calcium phosphates, as well as any insoluble calcium salts deriving from a mineral or organic acid.

The calcium derivatives of high purity according to the invention may be used for the preparation of food compositions (use of calcium citrate for baby milks) or of pharmaceutical compositions, manufacture of magnetic tapes, etc.

The present invention has still for subject matter a mixture of particles containing calcium in the form of oxide and/or hydroxide suitable for the working of a process according to the invention. This mixture contains at least one additive, for example:

from 0.5 to 10 parts by weight, preferably from 0.5 to 1 part by weight of silica per part by weight of CaO and/or $Ca(OH)_2$, and possibly less than 0.1 part by weight, preferably from 0.01 to 0.03 part by weight of alumina and/or zeolithe and/or iron (or iron derivatives) and/or other porous carriers per part by weight of CaO and/or $Ca(OH)_2$.

What we claim is:

1. Process for the preparation of vaterite in which a mixture of particles containing a compound selected from the group consisting of calcium oxide and calcium hydroxide is treated in a reaction medium containing an acid salt of an organic amine so as to convert the calcium into soluble salt and so as to obtain a medium, the pH of which -called pH of treatment- has a value higher than 10, while the calcium content of which is between 0.35 and 0.65 mole/litre; $CO_2$ is introduced into the medium subjected to a stirring so that the pH of the medium reaches a pH—called pH of saturation—, the value of which is about $0.83 \times pH$ of treatment, and $CO_2$ is introduced in the medium at a rate lower to 50 g $CO_2$/hour/litre so as to form substantially spherical vaterite.

2. Process according to claim 1, in which $CO_2$ is introduced in the medium when the calcium content of the medium is comprised between 0.45 and 0.55 mole/liter.

3. Process according to claim 1, in which $CO_2$ is introduced in the medium when the temperature of the medium is lower than 40° C.

4. Process according to claim 1 in which $CO_2$ is introduced into the medium in three steps, namely:
feeding $CO_2$ so as to lower the pH to a pH called pH of saturation, the value of which is about $0.83 \times$ pH of treatment;
feeding $CO_2$ at a rate less than 50 g $CO_2$/hour/liter so as to lower the pH to a pH, called pH of nucleation, the value of which is about $0.8 \times$ pH of treatment, and
feeding $CO_2$ at a rate lower than 50 g $CO_2$/hour/liter up to the lowering of the pH to a pH called pH of cristallization, the value of which is less than $0.75 \times$ pH of treatment,
these three steps being separated each from the other by an intermediate step in which no $CO_2$ is introduced into the medium.

5. Process according to claim 1, in which the mixture of particles containing calcium is treated at a temperature lower than 50° C.

6. Process according to claim 1, in which the reaction medium is submitted to a pressure higher than $2 \ 10^5$ Pa for the first step of feeding $CO_2$ into the medium.

7. Process according to claim 1, in which the medium is submitted to a vigorous stirring where $N_{Re} \geq 8000$ for the first step of feeding $CO_2$ into the medium.

8. Process according to claim 1, in which the medium is submitted to a moderate stirring where $N_{Re} \leq 5000$ for the second step of feeding $CO_2$ into the medium.

9. Process according to claim 1, in which the acid salt of organic amine is a compound of general formula 1

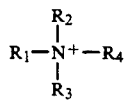

(1)

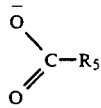

in which
at least one radical selected from the group consisting of $R_1$, $R_2$, $R_3$ and $R_4$ is selected from the group consisting of hydrocarbon group and hydrocarbon group substituted by at least one hydroxyl group.

10. Process according to claim 9 in which the acid salt of organic amine is a compound of formula 1 i which the radicals $R_1$, $R_2$, $R_3$, $R_4$ and $R_5$ have the following meanings:
$R_1$ is a hydrocarbon radical substituted by at least one hydroxyl group, this radical having 1 to 10 carbon atoms;
$R_2$, $R_3$ and $R_4$ are selected from the group consisting of hydrogen atom, hydrocarbon radical and hydrocarbon radical substituted by at least one hydroxyl group, and
$R_5$ is selected from the group consisting of hydrogen atom, $C_1$-$C_{10}$ hydrocarbon radical $C_1$-$C_{10}$ hydrocarbon radical substituted by at least one hydroxyl group and $C_1$-$C_{10}$ hydrocarbon radical substituted by at least one carboxyl group.

11. Process according to claim 9, in which the acid salt of formula 1 is selected from the group consisting of diethylamino acetate, diethylamino formate, monoethanoloamino acetate and monoethanolamino formate.

12. Process according to claim 1 in which insolubles are removed from the medium after the treatment of the mixture of particles with an acid salt of an organic amine.

13. Process according to claim 12, characterized in that the mixture of particles containing calcium is treated in the reaction medium containing an acid salt of an organic amine in presence of an additive selected among the group consisting of silica, alumina, iron, iron derivative, and zeolite.

14. Process according to claim 1, in which $CO_2$ is introduced in the medium when the temperature of the medium is lower than 20° C.

15. Process according to claim 1, in which $CO_2$ is introduced into the medium in three steps, namely:
feeding $CO_2$ so as to lower the pH to a pH called pH of saturation, the value of which is about $0.83 \times$ pH of treatment;
feeding $CO_2$ at a rate less than 50 g $CO_2$/hour/liter so as to lower the pH to a pH, called pH of nucleation the value of which is about $0.8 \times$ pH or treatment, and
feeding $CO_2$ at a rate lower than 50 g $CO_2$/hour/liter up to the lowering of the pH to a pH called pH of cristallization, comprised between 0.7 and $0.75 \times$ pH of treatment, these three steps being separated each from the other by an intermediate step in which no $CO_2$ is introduced into the medium.

16. Process according to claim 5, in which the mixture of particles containing calcium is treated at a temperature comprised between 20° and 30° C.

17. Vaterite obtained by the process according to claim 1, said vaterite having the form of sphere with two diametrically opposite hollows and a grain size distribution factor lower than 0.5, the grain size distribution factor being calculated by means of the following formula:

$$2 \times \frac{d_{80\%} - d_{20\%}}{d_{80\%} + d_{20\%}}$$

in which
$d_{80\%}$ is the upper diameter of the particles of the fraction of the mixture passing at 80%
$d_{20\%}$ is the upper diameter of the particles of the fraction of the mixture passing at 20%
fraction passing at x%
is the fraction containing the particles of the mixture having a size lower than a determined value, this fraction corresponding to x% by weight of the mixture.

18. Vaterite according to claim 17, having a size lower than $20\mu$.

19. Vaterite according to claim 17, having a mean size lower than $5\mu$.

20. Vaterite according to claim 17, having a mean size lower than $3\mu$.

21. Vaterite according to claim 17, provided with a layer of a metal selected among the precious metals.